United States Patent
Farritor et al.

(10) Patent No.: US 7,126,303 B2
(45) Date of Patent: Oct. 24, 2006

(54) ROBOT FOR SURGICAL APPLICATIONS

(75) Inventors: Shane Farritor, Lincoln, NE (US);
Dmitry Oleynikov, Omaha, NE (US);
Stephen R. Platt, Garland, NE (US);
Mark Rentschler, Omaha, NE (US);
Jason Dumpert, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 11/338,166

(22) Filed: Jan. 24, 2006

(65) Prior Publication Data
US 2006/0119304 A1    Jun. 8, 2006

Related U.S. Application Data

(63) Continuation-in-part of application No. 10/616,096, filed on Jul. 8, 2003, now Pat. No. 7,042,184.

(51) Int. Cl.
*B25J 5/00* (2006.01)

(52) U.S. Cl. .............................. 318/568.12; 318/568.11; 128/899; 104/138.2; 180/9.1; 600/114

(58) Field of Classification Search ........ 318/560–587; 104/138.2; 600/101, 114, 146, 478, 104, 600/434, 585, 407, 182; 901/1–3; 324/220; 166/66.5; 128/899; 138/98
See application file for complete search history.

(56) References Cited

U.S. PATENT DOCUMENTS

| | | | | |
|---|---|---|---|---|
| 4,568,311 A * | 2/1986 | Miyake | ...................... | 464/109 |
| 4,852,391 A * | 8/1989 | Ruch et al. | .............. | 73/40.5 R |
| 5,172,639 A * | 12/1992 | Wiesman et al. | ........ | 104/138.2 |
| 5,284,096 A * | 2/1994 | Pelrine et al. | ........... | 104/138.2 |
| 5,304,899 A * | 4/1994 | Sasaki et al. | ................. | 318/16 |
| 5,363,935 A * | 11/1994 | Schempf et al. | ............. | 180/9.1 |
| 5,382,885 A * | 1/1995 | Salcudean et al. | ..... | 318/568.11 |
| 5,388,528 A * | 2/1995 | Pelrine et al. | ................ | 105/78 |
| 5,736,821 A * | 4/1998 | Suyama | ....................... | 318/16 |
| 5,845,646 A * | 12/1998 | Lemelson | ................... | 128/899 |
| 5,878,783 A * | 3/1999 | Smart | .......................... | 138/93 |
| 6,031,371 A * | 2/2000 | Smart | ......................... | 324/220 |
| 6,058,323 A * | 5/2000 | Lemelson | ................... | 600/408 |
| 6,107,795 A * | 8/2000 | Smart | ........................ | 324/220 |
| 6,159,146 A * | 12/2000 | El Gazayerli | ............... | 600/106 |
| 6,162,171 A * | 12/2000 | Ng et al. | ..................... | 600/141 |
| 6,286,514 B1 * | 9/2001 | Lemelson | ................... | 128/899 |
| 6,293,282 B1 * | 9/2001 | Lemelson | ................... | 128/899 |
| 6,309,403 B1 * | 10/2001 | Minor et al. | ................. | 606/205 |
| 6,321,106 B1 * | 11/2001 | Lemelson | ................... | 600/407 |
| 6,327,492 B1 * | 12/2001 | Lemelson | ................... | 600/434 |
| 6,400,980 B1 * | 6/2002 | Lemelson | ................... | 600/478 |
| 6,450,104 B1 * | 9/2002 | Grant et al. | ............. | 104/138.2 |
| 6,468,203 B1 * | 10/2002 | Belson | ........................ | 600/146 |
| 6,512,345 B1 * | 1/2003 | Borenstein et al. | .... | 318/568.12 |
| 6,610,007 B1 * | 8/2003 | Belson et al. | ................ | 600/146 |
| 6,648,814 B1 * | 11/2003 | Kim et al. | ................... | 600/114 |
| 6,687,571 B1 * | 2/2004 | Byrne et al. | ................. | 700/245 |
| 6,702,734 B1 * | 3/2004 | Kim et al. | ................... | 600/114 |
| 6,719,684 B1 * | 4/2004 | Kim et al. | ................... | 600/101 |

(Continued)

*Primary Examiner*—Paul Ip
(74) *Attorney, Agent, or Firm*—Licata & Tyrrell P.C.

(57) ABSTRACT

The present invention provides a micro-robot for use inside the body during minimally-invasive surgery. The micro-robot includes an imaging devices, a manipulator, and in some embodiments a sensor.

23 Claims, 3 Drawing Sheets

U.S. PATENT DOCUMENTS

| | | | |
|---|---|---|---|
| 6,774,597 B1* | 8/2004 | Borenstein | 318/568.12 |
| 6,820,653 B1* | 11/2004 | Schempf et al. | 138/98 |
| 6,824,508 B1* | 11/2004 | Kim et al. | 600/101 |
| 6,824,510 B1* | 11/2004 | Kim et al. | 600/114 |
| 6,832,988 B1* | 12/2004 | Sproul | 600/459 |
| 6,870,343 B1* | 3/2005 | Borenstein et al. | 318/568.16 |
| 6,917,176 B1* | 7/2005 | Schempf et al. | 318/568.11 |
| 2001/0018591 A1* | 8/2001 | Brock et al. | 606/130 |
| 2002/0103417 A1* | 8/2002 | Gazdzinski | 600/109 |
| 2002/0111535 A1* | 8/2002 | Kim et al. | 600/158 |
| 2002/0120254 A1* | 8/2002 | Julian et al. | 606/1 |
| 2002/0140392 A1* | 10/2002 | Borenstein et al. | 318/568.12 |
| 2002/0156347 A1* | 10/2002 | Kim et al. | 600/160 |
| 2002/0171385 A1* | 11/2002 | Kim et al. | 318/568.12 |
| 2002/0190682 A1* | 12/2002 | Schempf et al. | 318/568.11 |
| 2003/0045888 A1* | 3/2003 | Brock et al. | 606/130 |
| 2003/0089267 A1* | 5/2003 | Ghorbel et al. | 104/138.1 |
| 2003/0092964 A1* | 5/2003 | Kim et al. | 600/101 |
| 2003/0167000 A1* | 9/2003 | Mullick et al. | 600/424 |
| 2003/0172871 A1* | 9/2003 | Scherer | 118/306 |
| 2003/0230372 A1* | 12/2003 | Schmidt | 156/64 |
| 2004/0099175 A1* | 5/2004 | Perrot et al. | 104/138.1 |
| 2004/0140786 A1* | 7/2004 | Borenstein | 318/568.12 |
| 2004/0173116 A1* | 9/2004 | Ghorbel et al. | 104/138.2 |
| 2004/0254680 A1* | 12/2004 | Sunaoshi | 700/253 |

* cited by examiner

ROBOT FOR SURGICAL APPLICATIONS

INTRODUCTION

This application is a continuation-in-part of U.S. patent application Ser. No. 10/616,096 filed Jul. 8, 2003, now U.S. Pat. No. 7,042.184 incorporated herein by reference in its entirety.

BACKGROUND OF THE INVENTION

Interest in micro-robotics has increased rapidly in recent years. This is due mainly to technology development in the fields of microelectronics, micromachining, and microactuation. Currently, it is possible to build and test miniature systems that include numerous features, including sensors, actuators, and embedded control subsystems. The trend toward miniaturization is seen not only in industrial applications, but in medical applications as well.

There are many industrial applications for micro-robots. Micro-robots are suitable for work in small and inaccessible places; for example, in dismantling and reassembling factory pipelines, inspection of small environments, measuring various parameters, miniature manipulation, repairs, micro-machining, complex molecular and atomic operations, and precision tooling, grasping, transport, and positioning with nanoscale motion resolution. Micro-robots that mimic insects have been developed, though currently such micro-robots are of limited use due to their size and low-level agility (see Fearing, R. S. et al. (2000) *Proceedings of the 2000 IEEE International Conference on Robotics and Automation* p. 1509–16). Mobile micro-robots, such as swimming robots, can be used for inspection and repair of thin pipes. Most of micro-robots concentrate on specific tasks. Micro-robots with small power requirements generally are suitable only for simple tasks, like moving forward and backward.

There are an increasing number of medical applications for micro-robots, such as in biological cell manipulation, blood-flow measurement, microsurgery of blood vessels and endoscopic surgery (a minimally invasive surgery). However, micro-robots have not been applied in laparoscopic or other minimally invasive surgery to date. Laparoscopic surgery avoids the trauma traditionally inflicted in gaining access to abdominal organs by using long, rigid instruments and cameras inserted into the body through small incisions. While minimally invasive surgical procedures reduce patient trauma, pain, recovery time, and hospital costs, there are several drawbacks to the technique. For example, there are regions of the patient that are inaccessible with current methods, and there is a lack of tactile feedback and limited dexterity and perception.

One micro-robot used currently in medical applications is a semi-autonomous endoscope device used during colonoscopy. The main advantage of this device is that the procedure generates only "internal" forces, unlike standard colonoscopy where the physician must provide high external forces to overcome acute intestinal bends. Two propulsion mechanisms have been proposed. One is based on "inchworm" locomotion, while the other uses "sliding clamper" locomotion (Menciassi et al. (2002) *Proceedings of the 2002 IEEE/RSJ International Conference on Intelligent Robots, EPFL* p. 1379–84).

Also, a miniature disposable imaging capsule has been developed. See, e.g., U.S. patent application Ser. No. 09/759,398. Such a capsule is swallowed by the patient and, with the natural movement of bowel, it moves through the gastrointestinal tract, and is passed naturally out of the body. The capsule transmits information (such as imaging information) to a receiver worn by the patient, which is later processed on a computer. The capsule consists of optical dome, lens holder, lens, illuminating LEDs, CMOS imager, battery, transmitter, and antenna. This device is used for colonoscopy. A similar device that is radio-controlled allowing for limited movement has been tested by researcher Annette Fritscher-Ravens at the University of London.

A device similar to that of Menciassi, et al., which is electro-pneumatically driven, has been developed. The advantage of this micro-robot is that it minimizes the contact between the colonoscope and the interior boundary of the colon, which makes the progression of colonoscope easier. The design uses three metal bellows disposed 120 degrees apart, while the position in the intestine is driven by three sensors positioned on a superior plate (Thoman et al. (2002) *Proceedings of the 2002 IEEE/RSJ International Conference on Intelligent Robots, EPFL*, p. 1385–90).

A Japanese company has developed miniature prototypes of endoscopic tools. One is an autonomous endoscope that can move through a patient's veins. Another prototype is catheter mounted with a tactile sensor to examine tumors for malignancy.

A prototype of a micro-catheter with active guide wire has been proposed. The active guide wires consist of hollow cable, and have two bending degrees of freedom (DOF) using an ionic conduction polymer film (ICPF) actuator on the front end. Use of an ICPF actuator provides the catheter with flexibility, good response, low voltage and safety (Guo et al. (1996) *Proceedings of the 1996 IEEE International Conference on Robots and Automation* (3):2226–31). A shape memory alloy (SMA) actuator has been proposed as well, but has some disadvantages, such as cooling, leaking electric current, and response delay (Fukuda et al. (1994) *Proceedings of the 1994 IEEE International Conference on Robotics and Automation* p. 418–23).

In addition, an ICPF actuator used in a fish-like robot having three degrees of freedom has been proposed for use in procedures involving aqueous media such as blood. The actuator is used as a propulsion tail fin and a buoyancy adjuster. The moving motion (forward, right, or left) is manipulated by changing the frequency of the applied voltage. The device is 45 mm long, 10 mm wide, and 4 mm thick, and might be used in microsurgery of blood vessels (Guo et al. (2002) *Proceedings of the 2002 IEEE International Conference on Robotics and Automation* p. 738–43). See also Mei et al. (2002) *Proceedings of the 2002 International Conference on Robotics and Automation* p. 1131–36.

A spiral-type magnetic swimming micro-machine has been developed. This device is driven by a rotating magnetic field, which implies that the system is wireless and does not require batteries of any kind. The micro-machine is composed of a cylindrical NdFeB magnet, ceramic pipes, and a spiral blade. The prototype length is 15 mm with a 1.2 mm diameter. It was shown that the device is suitable for miniaturization. The swimming direction of the machine can be controlled by changing the direction of the rotational magnetic field, while the velocity can be adjusted by changing the frequency of the rotating magnetic field. Tests have shown that in addition to running in a blood-like environment, the micro-machine has potential use in human organs (Ishiyama et al. (2000) *International Symposium on Micromechatronics and Human Science* p. 65–69).

Micro-robots are being used for performing automatic DNA injection autonomously and semi-autonomously through a hybrid visual serving control scheme. The system comprises an injection unit, an imaging unit, a vacuum unit, a microfabricated unit, and a software unit. A high precision, three DOF micro-robot is a part of the injection unit. The micro-robot is used to place precisely the injection pipette. In addition to being able to perform pronuclei DNA injection, the system is suitable for performing intracytoplasmic injection (Yu and Nelson (2001) *Proceedings of the* 2001 *IEEE International Conference on Robotics and Automation* p. 620–25).

There remains a need in the art for micro-robots that allow one to treat pathological organs while preserving healthy tissues, yet provide dexterity enhancement, enhanced perception, improved access, and remote treatment capabilities. The present invention fulfills this need in the art.

SUMMARY OF THE INVENTION

The robot of the present invention provides a mobile robotic system to be used inside the body in minimally invasive surgery, particularly laparoscopy. The robot according to the present invention is equipped with biopsy graspers. In particular embodiments, the instant robot also contains various sensors including, but not limited to, imaging devices and/or sensors to measure temperature, blood or other fluids in tissue, humidity, pressure and/or pH. In addition, the robot comprises one or more transceivers. Certain embodiments of the instant robot provide for adaptation to fit through standard laparoscopic tools for use in the abdomen during laparoscopic surgery. The invention provides both wired and wireless embodiments.

Thus, the present invention provides robots for performing minimally-invasive surgery inside the body, including human bodies, where the robots comprise a body; mobilization means such as wheels or tracks for moving the robot; controller means for remotely controlling the mobilization means; an actuator; a power supply; a means for obtaining a biopsy sample; and in particular embodiments an adjustable-focus camera or imaging device. The robot of the present invention can, in various embodiments, take on many different configurations, such as cylindrical or spherical shapes, or, alternatively, a shape such as that of a small vehicle. The robot of the present invention in one embodiment is tethered or wired, and in another embodiment, it is wireless. When the robot is wireless, an internal power supply is used, and the robot further comprises a receiver and a transmitter. The robot can use any type of compatible actuator. Also, another embodiment of the invention embraces a system for use inside an animal body, wherein the system employs a laparoscopic surgical tool, wherein the robot is adapted to fit through the port of the laparoscopic surgical tool; a robot body, an adjustable-focus camera or imaging device, a means for obtaining a biopsy sample, a mobilization means to move the robot transverse to a length of the robot, a controller to remotely control the mobilization means, an actuator and a power supply.

The sensor devices of the present invention include those that sense pH, temperature, gasses, fluids such as blood, electrical potential, heart rate, fluid composition, respiration rate or humidity. Another embodiment of the present invention provides use of the robot of the present invention inside the body in minimally-invasive surgical applications.

BRIEF DESCRIPTION OF THE DRAWINGS

FIG. 2A shows the dimensions (a, b, c, d, g, f, and h) and measurable cutting forces ($F_{tip}$ and $F_{cable}$) of biopsy forceps. FIG. 2B shows modifications made to off-the-shelf biopsy forceps, including cutting the tube and wires to place a load cell in series with the actuation wire, to measure cutting forces.

DETAILED DESCRIPTION OF THE INVENTION

Figure 1:
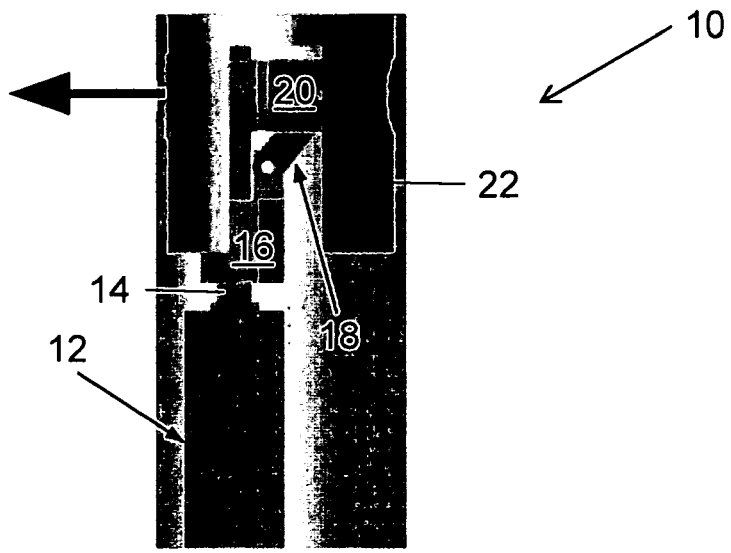
FIG. 1 shows a CAD drawing of the actuation mechanism 10 implemented in the biopsy robot of the present invention.

A more particular description of the invention, briefly summarized above, can be had by reference to the embodiments of the invention described in the present specification and illustrated in the appended drawings. It is to be noted, however, that the specification and appended drawings illustrate only certain embodiments of this invention and are, therefore, not to be considered limiting of its scope. The invention may admit to equally effective embodiments.

Reference will now be made in detail to exemplary embodiments of the invention. While the invention will be described in conjunction with these embodiments, it is to be understood that the described embodiments are not intended to limit the invention solely and specifically to only those embodiments. On the contrary, the invention is intended to cover alternatives, modifications, and equivalents that may be included within the spirit and scope of the invention as defined by the attached claims.

The increased use of laparoscopy has led to a dramatic shift in surgical methods and improvements in patient care. Laparoscopic surgery avoids the trauma traditionally inflicted in gaining access to the abdominal organs by using long, rigid instruments and cameras inserted into the body through small incisions. Maneuvering space for the tools used is created by insufflating $CO_2$ to lift the abdominal wall away from the organs. The reduced surgical invasiveness in laparoscopic surgery results in fewer complications and a more rapid recovery for the patient. The adoption of laparoscopic techniques has been driven by technological advances such as imaging systems and, recently, robots. Surgical laparoscopic robots currently are used to maneuver and position instruments with high precision and allow micro-scale tasks otherwise not possible. Despite these successes, however, laparoscopy remains constrained in application due to the loss of sensory feedback, limited imaging and the reduced mobility and dexterity associated with current approaches.

The present invention facilitates the application of laparoscopy and other minimally invasive surgical techniques to a much wider range of procedures by providing semi-autonomous and autonomous remotely controlled robots, also referred to herein as micro-robots, that are used inside the body, especially human bodies. The present invention provides robotic in vivo wired and wireless manipulator, imaging and sensor devices that are implanted in the area to be treated, for example, the abdomen. The devices overcome the limitations associated with current generation laparoscopic cameras and tools, providing the surgical team a view of the surgical field from multiple angles, in vivo patient monitoring capability and in vivo manipulator dexterity. It is contemplated that the instant in vivo robot could help the surgeon directly manipulate tissue; thereby leading to a family of robots that could be placed in vivo to perform a task collectively while being remotely controlled. A camera robot could provide the visual feedback to the surgeon, while a grasper robot retracts the tissue and third robot performs the dissection.

In accordance with the instant invention, one embodiment embraces a robot with one or more image sensors to increase the view of the body cavity for the surgical team. Current laparoscopes use rigid, single view cameras inserted through a small incision. The camera has a limited field of view and its motion is highly constrained. To obtain a new perspective using this prior art technique often requires the removal and reinsertion of the camera through another incision, increasing patient risk. Instead, the present invention provides one or more robots inside the body to deliver additional body cavity images that improve the surgeon's geometric understanding of the surgical area.

As used in the context of the present invention, the term "camera" or "imaging device" describes the imaging elements and processing circuitry which is used to produce a video signal which can be accepted by a standard video device such as a television or video monitor accompanying a personal computer. The term "image sensor" as used herein describes the components of a solid state imaging device which captures images and stores them within the structure of each of the pixels in the array of pixels found in the imaging device. The terms "signal" or "image signal" as used herein, and unless otherwise more specifically defined, refer to an image which at some point during its processing by the imaging device, is found in the form of electrons which have been placed in a specific format or domain. The term "processing circuitry" as used herein refers to the electronic components within the imaging device which receive the image signal from the image sensor and ultimately place the image signal in a usable format. The terms "timing and control circuits" or "circuitry" as used herein refer to the electronic components which control the release of the image signal from the pixel array.

For such a camera or imaging device to be useful, the camera must have adequate resolution, field-of-view, and lighting, and alternatively, depth of field and range of focus, to show details important to the operator. Miniature cameras are commonly found in devices such as cellular phones and endoscopic. In this regard, the camera of the present invention can be any known in the art that is compatible with the various designs and configurations of the invention. For example, the camera or imaging device of the present micro-robot can employ any common solid state image sensor including a charged coupled device (CCD), charge injection device (CID), photo diode array (PDA), or complementary metal oxide semiconductor (CMOS), which offers functionality with simplified system interfacing. For example, a particularly suitable CMOS imager including active pixel-type arrays is disclosed in U.S. Pat. No. 5,471,515. This CMOS imager can incorporate a number of other different electronic controls that are usually found on multiple circuit boards of much larger size. For example, timing circuits, and special functions such as zoom and anti-jitter controls can be placed on the same circuit board containing the CMOS pixel array without significantly increasing the overall size of the host circuit board. Furthermore, this particular CMOS imager requires 100 times less power than a CCD-type imager. The CMOS imager disclosed in U.S. Pat. No. 5,471,515 has enabled the development of a "camera on a chip." As such, many CMOS imagers can be manufactured at a fraction of the cost of other solid state imaging technologies. Suni Microsystems, Inc. (Mountain View, Calif.) has also developed a CCD/CMOS hybrid which combines the high quality image processing of CCDs with standard CMOS circuitry construction. In particular embodiments, the camera is a CMOS camera. In other embodiments, the camera has a defined focal length, which is manually adjusted or mechanically actuated by adjustable-focus camera means.

A variety of adjustable-focus mechanisms are known in the art and suitable for actuating focusing in accord with the present invention. For example, one basic design employs the use of a motor and a lead screw. The motor turns a turn-table that is attached to a lead screw. A mating nut is attached to the imager. As the lead screw turns the imager translates toward and away from the lens that is mounted to the body of the robot. Alternatively, a more rigid actuation mechanism 10 as depicted in FIG. 1 employs a motor 12 that is directly connected to a lead screw 14 which is rotated by motor 12. As the lead screw 14 rotates it drives a lead nut 16 up and down. This up and down motion is translated by a linkage 18 to a slider 20 that moves left to right. Slider 20 is held in place by a mechanism housing or guide 22. A lens or image sensor mounted to slider 20 can be translated back and forth from left to right to allow adjustable focusing. In particular embodiments, the adjustable-focus camera and biopsy mechanism are actuated by a rotary-to-translatory mechanism using one motor.

The image sensor can be controlled externally to adjust image quality (e.g., color hues, white balance, saturation, etc.) to provide quality feedback in conditions of low lighting. Similarly, focus adjustment and the biopsy commands are provided externally using a control box, while wheel commands are provided using a joystick.

In yet another embodiment of the present invention other sensors are provided, such as those that measure, for example, temperature, pressure, presence of various gases and/or humidity or other parameters. Current minimally invasive surgical techniques, due to their remote nature, decrease the surgeon's ability to sense the surgical environment. The sensor-equipped robot according to embodiments of the present invention restores the surgeon's ability to perform more complex procedures and more accurately monitor patient health.

The robot of the invention further contains one or more manipulators that assist the surgeon in tasks requiring high dexterity. Exemplary manipulators include, but are not limited to, clamps, scalpels, biopsy graspers, forceps, and the like. In particular embodiments, the instant robot is equipped with a means for obtaining a biopsy sample. For example, the biopsy sample can be obtained with biopsy forceps or graspers at the tip or end of a folding or retractable manipulator arm.

As disclosed herein, a novel mechanism has been developed for generating high forces required to cut biopsy samples. The actuation mechanism employs a linkage, which upon reaching singularity, generates a sufficient magnitude of drawbar force (i.e., greater than 0.6 N) to sever living tissue. Accordingly, not only is this actuation mechanism useful in accordance with the instant biopsy means, this actuation mechanism finds application in a variety of other surgical tools and tasks including, but not limited to, clamping, stapling, cutting, cauterizing, ultrasonically burning, and the like. Thus, it is contemplated that laparoscopic and surgical tools routinely used in the art can be modified to incorporate this mechanism.

The present invention is novel as it applies in vivo mobile robots in minimally invasive surgery, such as laparoscopy. Previous integration of surgery and robots has involved large robots on the outside of the patient, such as those sold by Intuitive Surgical, Inc. (Sunnyvale, Calif.) and described by Ruurda, J. P., et al. (2002) *Ann. R. Coll Surg. Engl.* 84:223–226. The use of micro-robots in vivo represents a fundamental paradigm shift in robot-assisted surgery.

The present invention provides robotic wired and wireless manipulator, imaging and sensor devices for use in vivo. The robots can take on any configuration and be equipped with any number of sensors, manipulators or imaging devices. There are hundreds of different components known in the art of robotics that can be used in the construction of the micro-robots of the present invention; for example, there are hundreds controllers, motors, power supplies, wheels, bodies, receivers, transmitters, cameras, manipulators, and sensing devices that can be used in various combinations to construct micro-robots according to the present invention.

Controllers can be purchased off-the-shelf, constructed de novo, or off-the-shelf controllers can be customized to control the robotic components of the present invention. One skilled in the art would be able to select a controller appropriate for the micro-robot or manipulators according to the present invention in view of the exemplary controllers disclosed herein.

Likewise, actuators useful in the present invention can be of many types. For example, the mobile robot of the present invention can use a Nakamishi brushless direct current motor that has been used commonly in robotic and other applications. These motors require external communication, generally performed by a circuit supplied by the manufacturer. The manipulator of the micro-robot exemplified herein used a permanent magnet DC motor made by MicroMo™ Electronics, Inc. (Clearwater, Fla.). Permanent magnet DC motors are commonly used devices. However, other devices would be useful in alternative embodiments of the present invention, including shape memory alloys, piezoelectric-based actuators, pneumatic motors, or hydraulic motors, or the like. Pneumatic and hydraulic motors are efficient, but the pump generally must be external to the robot. Thus, such motors can be useful in a tethered or wired embodiment of the present invention, but not in the wireless embodiment of the present invention.

When selecting a power supply, an external power supply can be employed with a tethered configuration; however, particular embodiments embrace that the power be supplied by batteries. Versions of the robot and/or manipulator of the present invention can use alkaline, lithium, nickel-cadmium, or any other type of battery known in the art. Alternatively, magnetic induction is another possible source of power, as is piezoelectrics. In addition, one of skill in the art could adapt other power sources such as nuclear, fluid dynamic, solar or the like to power the micro-robots of the present invention.

A distinctive feature of the present invention is its mobility. The embodiment detailed in the Example herein used treaded wheels for mobility; however, the present invention also contemplates use of alternative methods of mobility such as walking robots, treads or tracks (such as used in tanks), hybrid devices that include combinations of both wheels and legs, inchworm or snake configurations that move by contorting the body of the robot, and the like. The wheels used on the mobile micro-robot described herein were made out of aluminum and rubber; however, virtually any material can be used to construct the wheel or other mobility-creating element as long as sufficient traction is obtained. The wheel shape used herein was a round, tubular-type treaded configuration; however, again, virtually any configuration could be employed, e.g., round, square, spherical, or triangular, as long as sufficient traction is obtained and trauma to the areas traversed are minimized.

In accordance with the exemplary micro-robot disclosed herein, it was unexpectedly found that in order to obtain sufficient traction to move a wheeled micro-robot (i.e., a robot small enough to maneuver within the body cavity) on the wet surfaces inside the body, the wheels require tread and the wheel size be maximized. In this regard, particular embodiments embrace a micro-robot wherein at least 80% of the micro-robot surface area is covered with treaded wheels. In other embodiments, up to 98% of the micro-robot surface area is covered with treaded wheels. In still other embodiments, 80–98% of the micro-robot surface area is covered with treaded wheels.

Receivers and transmitters useful in the present invention are many, such as those used on remote locks, such as for cars and other vehicles, other remote controls, and receiver and transmitter elements used in cell phones. Essentially, the input to the robot would be user command signals to the device, for example, to move various components such as the device itself, or for positioning the camera, sensor components or manipulator. The output from the robot would be primarily data from the video or sensors.

The mobile micro-robot of the present invention was cylinder-shaped so as to be compatible with laparoscopic tools known currently in the art. However, as with the other components, the body configuration of robots according to the present invention is not limited to the mobile micro-robot presented in the Example herein. Indeed, the only constraints on the shape of the body of the robot in various embodiments are that the body be able to incorporate the imaging, sensor and/or manipulator components required; not affect adversely the traction required; or cause trauma to the areas of the body traversed.

In addition to the imaging device, the instant micro-robot can further provide other sensing capabilities. Sensor devices can be any of those used in the art compatible with the small size of the robot. For example, various sensors for temperature, pH, $CO_2$, other gasses, electrical potential, heart rate, respiration, humidity and the like are known and are available commercially. As with the body configuration, any camera or imaging device, or sensor can be used as long as it does not affect adversely traction or the safety of the patient.

Further, manipulators according to the present invention can be, like the prototype presented in the Example herein, modified versions of off-the-shelf surgical tools, or alternatively, manipulators of the present invention can be constructed de novo. The manipulators according to the present invention are small compared to traditional manipulators, and can come in any shape as long as it does not affect adversely traction of the device or the safety of the patient, and as long as it is able to accomplish the tasks required in the surgical manipulation.

Traditionally, a biopsy is performed with multiple ports, e.g., one for the camera and one for the tool. When applying a mobile robot of the present invention, the micro-robot is inserted into the abdominal cavity through one standard laparoscopic port, thereby eliminating at least one port. This significant improvement in the art would reduce patient trauma and facilitate the use of laparoscopy over other current systems.

The invention is described in greater detail by the following non-limiting examples.

EXAMPLE 1

Mobile Mini-Robot

The constraints placed on the size of the micro-robot according to the present invention were factors in determining the size and shape of the initial prototype of the embodiment described herein. Also simplicity of design, stability of the platform were considered. The mobile robot was constructed to be cylindrical in shape, with the wheels of the mobile robot covering most of the body. The robot's diameter was designed to be less than 15 mm so as to be able to, in this embodiment, fit through a port in a tool that is currently used in laparoscopic surgical techniques.

The size and function of this robot dictated also the use of very small electric motors. The first motors tested were motors that are used to vibrate pagers and mobile phones; however, these motors were found to be inadequate to supply the torque needed to move the robot. A suitable motor was selected. The electronics selected initially consisted of a modified control chip for the brushless motors that were selected. After control for the motors was established, the motors were wired to a game controller consisting of two joysticks. Each wheel on the robot was controlled by a separate joystick The first test of the robot was to use it to perform surgery in a pig. From this test it was found that there was insufficient traction to move the robot on the wet surfaces inside the body. This test resulted in a search for alternative wheel materials and wheel configuration. A second set of testing was then done in the lab, focusing on the incline that the robot was capable of climbing. Friction tests were done to find the frictional forces between the current aluminum wheels and several different surfaces The most critical and unusual aspect of this embodiment of the robot is its size. The size limitation is what distinguishes this micro-robot design from any other robot known in the art and drove the initial design constraints. Since the mobile robot was designed, in this embodiment, to be inserted through a standard 15 mm medical port, an overall cylindrical configuration was determined to maximize the allowable space. Therefore, as a starting point, the mobile robot was roughly cylindrical with a 15 mm outside diameter. As the internal components become better defined through testing, the outside diameter could be reduced if needed. The overall length of the device was less of a priority. Smaller was assumed to be better, but lacking a hard constraint, the length was left initially undefined.

After physical size, the next priority was that the device be easy to control by an operator, most likely a surgeon. The micro-robot, for example, must be able to move about the abdominal cavity of a human being and transmit real-time video without being a distraction to the surgeon.

The robot was designed to be able to move forward, backward, and turn in the smallest circle possible. Because of the cylindrical configuration of the device, a two-wheeled vehicle was chosen. In forward or backward motion, both wheels rotate at the same speed. To turn, this embodiment of the two-wheel mobile robot used skid steering to turn like a tank, the motors rotating at different speeds and/or directions. In this embodiment, where each wheel must be controlled individually, each wheel was given its own motor. However, two wheels are not enough to achieve the required motion. Since the wheels are coaxial, their rotation alone will not translate the robot across a surface without some non-rotating element in the robot. Because of this, the robot had to have some sort of "tail", something that would contact the surface and convert rotational motion into translational motion. The tail was mounted to the main body of the robot between the wheels.

Throughout the operation of this embodiment of the robot, it was desired that the operator would be provided with real-time video from an on-board camera or imaging device. For such a camera or imaging device to be useful, it would need to have adequate resolution, field-of-view and lighting to show details important to the operator. A square 7 mm camera was chosen that met the video requirements and would fit within the robot body. To assure adequate lighting, an LED was chosen to provide a constant (but potentially variable) source of illumination for the camera.

The camera's view must be steady while the robot moves so that situational awareness is maintained and the operator does not get lost within the body. In some embodiments, the camera points in the same direction relative to the robot, and the operator steers the robot to change the view location or perspective. In other embodiments, the camera position can be varied relative to the robot as needed by the operator. Since the center section of the robot body is limited to pure translation by the tail, mounting both the camera and LED onto the main body of the robot was the logical choice for this embodiment.

In some embodiments, the mobile robot is completely wireless and self-contained. Wiring from outside in some situations might limit the usefulness of the device, as well as reduce its mobility. A wireless embodiment of the micro-robot of the present invention must carry its own power source to operate the motors and the camera. Such a power source may take the form, for example, of very small batteries. In addition, a wireless embodiment requires that the motors include a wireless receiver to receive commands from the operator.

Another obvious consideration in the design and operation of the robot was that the robot be safe to the patient. Components were selected that did not have sharp edges. Additionally, excessive movement optimally should be avoided. Moreover, biocompatible materials had to be selected, and, in addition, the materials had to be easy to sterilize. Further, the materials comprising the micro-robot had to be sturdy enough so that the materials would not break inside the patient.

The mobile robot of the present invention is required to traverse a very unusual and irregular surface. The robot is required to drive across many different internal organs such as the liver, stomach, intestines, each of which has different surface properties. Some of these organs are soft and pliant, with a slippery exterior. Traction was an initial concern for the mobile robot. Moreover, the robot had to be designed such that it would not become high-centered on the tail or on the non-rotating center section. The initial robot concept countered this problem by minimizing the center area that contacted the organ surfaces.

Even with full contact upon the wheels, the robot had to overcome difficulties with the surfaces. For example, some of the organs are so soft that the robot tends to sink far below the original surface, placing it inside a deep valley or pouch out of which the robot must climb. In addition, each wheel had to be able to produce enough shear torque against the internal organs to move as required while not damaging the organs.

Based upon the criteria described, an initial concept was graphically created using solid modeling and component assembly. The main body of the initial device was made up of two nearly identical halves. The camera and LED were mounted to the top half, while the tail extended from the bottom half. The central space within the body housed two batteries and the electronic components required to control the motors and transmit the video signal. The motors were held in the slots at each end of the body. The wheels were designed to be as long as possible to minimize surface contact with the center section. Nylon bushings were used to support the inside diameter of the wheels and prevent wobble. The bushings were a light press fit with the body halves and had a smooth running fit with the wheels. The wheels had a line-to-line fit with the motor shafts To assemble the robot, the LED and camera were attached to the top half of the body. Next, the batteries, motors, tail and other electronic components were installed into the bottom half of the body. The two body halves were brought together and a nylon bushing was pressed over each end. The motors and batteries were held tightly within the body. Finally, the wheels were pressed onto the motor shafts.

Due to the very small size and relative complexity of the main body, machining appeared to be an unlikely method of fabrication. The only remaining inexpensive, rapid prototyping method was stereolithography. The wheels were to be turned from a solid aluminum bar. Any number of flexible materials could be used for the tail.

There were several factors that had to be taken into consideration when selecting which motors should be used for the mobile robot. These factors included the size of the motor and the torque that the motor could provide for the movement of the robot. The size of the motors was limited by the overall size and shape of the mobile robot. The mobile robot design in this embodiment had a small cylindrical shaped robot with the wheels covering most of the robot body. The robot was to have a maximum diameter of 15 mm and as short of a length as possible, optimally, less than 90 mm.

For the robot to meet the diameter restraint, the motor that was chosen had to have a diameter of less than 10 mm so that the motor would fit easily into the body. To meet the goal of a body length of less than 90 mm, a motor that was shorter than 30 mm was selected to ensure that there would be room the for batteries and electronics.

The next step in choosing a motor was to determine how much torque would be needed to move the robot. To calculate the needed torque, a free-body diagram of the robot sitting motionless on a slope was used to calculate the torque required to keep the robot stationary on the slope. This calculation would be the stall torque that the motor would need (provided that the friction of the surface was enough to prevent the wheels from slipping).

After determining what torque was required to move the robot, a motor and a gearhead were selected that would reduce the speed and increase the torque output from the motor. The first choice in motors for the prototypes was motors that were inexpensive and could be purchased off the shelf. Two motors that were inexpensive and on hand were tested to determine if they met the torque requirements. The first motor was a 6 mm diameter pager motor and the second was a 6 mm ZipZap motor (blue motor). Tests determined the stall torque of the motor per volt input.

For the test, a bar was placed on the motor shaft and a voltage was applied to the motor. The angle at which the bar stalled was then measured for each applied voltage. The torque that was present on the motor shaft was calculated and plotted versus the voltage, and a linear fit was used to determine the stall torque/volt of the motor.

The results of this test showed that neither the pager motor nor the ZipZap motor could have supplied enough torque to hold the mobile robot on more than a minimal slope. The ZipZap motor can provide 0.057 [mNm] at 3 V and the pager motor can supply 0.084 [mNm] at 3 V. Both motors could only hold the robot stationary on a 15 degree slope. The motor that was finally chosen for the prototype was one made by Namiki, model SBLO4-0829 with gearhead PG04-337. The motor runs on a nominal 3 V and can provide 10.6 [mNm] stall torque at 80 rpm. This motor provides a design factor of 4 for the robot on a 75-degree slope (if frictional force is sufficient to prevent sliding).

The motors chosen for this prototype included a control board, which needed a +5 V supply. The rotational speed of the motor was controlled with a potentiometer that acted as a voltage divider. For example, if the input to the motor was 0 V, the motor would not rotate, if the input was 5 V, the motor would rotate at top operational speed (according to the product specs). The relationship between voltage and speed was not linear, as the motor didn't start rotating until the voltage reaches more than 1.5 V.

The potentiometer on the control board had three terminals. The resistance between the two base terminals was a constant 1.021 k Ohms. The resistance between each base terminal and the third terminal was dependent on the position of the adjustment screw; if the screw was turned clockwise, one resistance increased, while the other decreased. If the screw was turned counterclockwise, the opposite was true. In both cases, the sum of the two resistances was always 1.021 k Ohms. It is this relationship between the terminals that created the voltage divider.

In addition to controlling speed of the motor, the control board allowed for the direction of rotation to be changed. One of the inputs to the board accepted a logic signal (0 or +5 V). If the signal was a logic "0", the motor spun in one direction. If the signal was a logic "1", the motor spun in the other direction.

It was clear to see that using a screwdriver to alter the speed of the motors was not a practical method of control. Thus, thumb sticks on a Playstation™ Dual-Shock controller were used to operate the motors. Each Playstation™ controller had two analog thumb sticks, each with two degrees of freedom. This essentially allowed the operator to move the thumbsticks a finite amount in an XY coordinate plane (though truly it was an X- and Y-rotation, it was so limited that the stick basically stayed in the XY plane). Each direction (X and Y) was controlled by a separate potentiometer; thus, pushing the stick forward a little yielded a different output than pushing the stick forward a great deal.

This method of control described herein is far superior to a directional pad (or D-pad). A D-pad type of control can be found on the original Nintendo™ game system. The pad looks like a plus sign (+), and has four discrete directions. For example, if one pushes up on the pad, the result is a logic "1" in that direction. Such a method of control works fine if one has no need for speed control. With an analog thumb stick, instead of all or nothing, movement can be sped up or slowed down according to how far the stick is pushed in the corresponding direction. This type of control is what was needed for the motors for this embodiment of this invention. However, as each motor had only one degree of rotational freedom, only one degree was needed for each of the thumb sticks. Thus, only the Y direction potentiometer was used.

To connect the Playstation™ controller, each potentiometer on the motor control boards was removed. A triangular resistor network was then created for each motor where the thumb sticks comprised one side and 1 k resistors comprised the other two sides. These networks were then soldered onto the control boards. When power was applied to the control board, the speed of each motor could be increased by pushing the respective thumb stick forward. Another feature of the Playstation™ controller was the "Z" button. Each controller had two buttons that were pushed by depressing the thumb sticks. Each thumb stick had three degrees of freedom: X- and Y-rotation, and translation in the Z-direction (albeit limited translation as it is a digital button). This button on the controller turned out to be quite useful as it was wired to control the direction of each motor. By connecting +5 v to one side of the button and the other side to the control board, it was possible to choose in which direction the motors rotated, push the thumb stick forward and the motor spun one way; push the thumb stick in, and then forward, and the motor spun the other way.

Next, a circuit was designed that allowed the user to push the thumb sticks forward to make the wheels spin forward, and backward to make the wheels spin backward, so that the thumb sticks no longer had to be depressed to change direction. The new design allowed a greater range of speed control and the ability to compensate for motor operational differences. The new design was much more complex than the control setup used in the initial prototypes, making control of the robot much easier Testing was conducted on the mobile robot. The weight of the robot, W, was 1.0 oz. The radius of the two wheels was 7.5 mm, and they were made of aluminum. Experiments were conducted on top of four types of objects: a tabletop, a mouse pad, particleboard and sliced beef liver. The robot was placed on top of each of these objects and the maximum friction force, F, was measured. The force was measured using an Ohaus Spring Scale with one-quarter ounce divisions. The force was approximated to the nearest 0.05 ounces. The coefficient of friction was determined by the formula $\mu=F/W$. Table 1 shows the four coefficients of friction measured by experiments.

TABLE 1

| | Maximum Friction Force (oz.) | Coefficient of Friction |
|---|---|---|
| Table | 0.05 | 0.050 |
| Mouse Pad | 0.65 | 0.65 |
| Particle board | 0.2 | 0.2 |
| Beef liver | 0.1 | 0.1 |

The robot was driven on a slope, which was increased from zero degrees until the robot could no longer move. The result showed that the practical maximum angle of slope was about 40 degrees. There was enough torque in the motors to power the robot at higher angles, but the friction between the wheels and the surface was not great enough to allow the robot to maintain traction once the slope got above 40 degrees.

The performance of the robot was tested in the body of a pig, and problems were encountered due to the lack of traction of the robot on the organs, and due to the softness of the organs. Mainly the problems resulted from the lack of frictional force, that is, the friction was not high enough to provide resistance to the torque provided by the wheel motor. In order to give the robot the capability to move well on a smooth, sloped or bumpy surface, the frictional force needed to be increased. From the force analysis, it was determined that the frictional force was proportional to the weight and inversely proportional to the radius of the wheel. Therefore, the following two methods are feasible and may be adopted. First, the mass of the robot could be increased. One good way to do so is to change the material of the wheels. In the initial design, aluminum was used which made the robot lighter than if steel had been used. Second, the radius of the wheels might be reduced. A smaller radius of the wheels also would increase the frictional force. The radius of the wheels could be reduced in a couple of ways. First, the wheels might be designed to have a smaller diameter; however, this solution is not the optimal solution as the space for the motor and electrical components is minimal and a smaller wheel diameter would reduce this space even further. Another solution is to add treads to the wheels. Alternatively, the tips of the treads may have a smaller radius without reducing the diameter of the wheel itself.

EXAMPLE 2

Biopsy Micro-Robot Design

To establish the required clamping and drawbar forces necessary for successful biopsy, experimental biopsies were conducted. A biopsy forceps device that is commonly used for tissue sampling during esophago-gastroduodenoscopy (EGD) and colonoscopies was modified to measure cutting forces during tissue biopsy. These forceps 30, shown schematically in FIG. 2A, were composed of a grasper 32 on the distal end with a handle/lever system 34 on the proximal end. A flexible tube 36 was affixed to one side of the handle 34 and the other end was attached to the fulcrum point 38 of the biopsy grasper 32. A wire 40 enclosed in plastic (Teflon®) inside tube 36 was used to actuate the grasper 32. This wire 40 was affixed to the free end of the handle lever 34 and at the other end to the end of the grasper lever arm 42. Actuation of the handle lever 34 caused wire 40 to translate relative to the tube 36 and actuate the biopsy graspers 32. The tip of the forceps was equipped with a small spike 44 that penetrated the tissue during sampling.

Figure 2A:
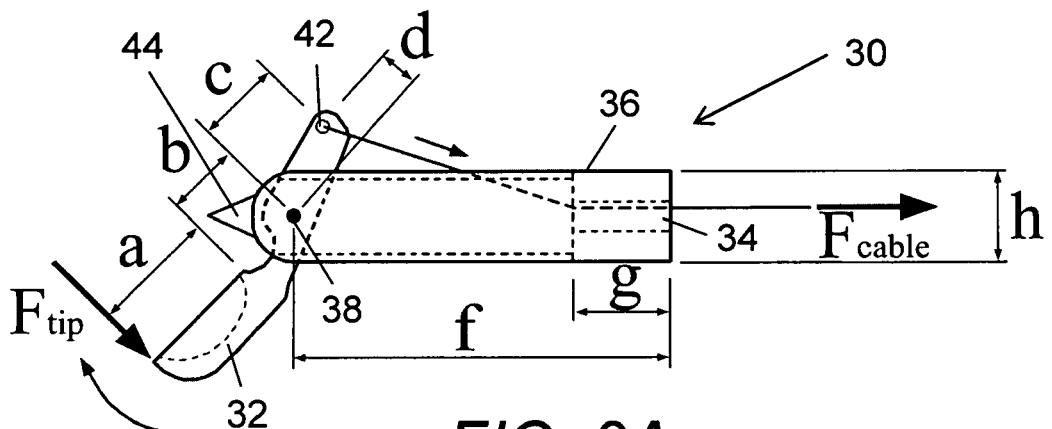
FIGS. 2A and 2B show schematics of a biopsy forceps.

The diameter of the forceps (h) was 2.4 mm (FIG. 2A). The dimensions of c, g and f were 2.1 mm, 2.0 mm, and 6.7 mm, respectively. The force at the tip of the grasper when the forceps were nearly closed was a function of the geometric design of the forceps.

$$F_{tip} = F_{cable}\left(\frac{d}{a+b}\right) \quad (1)$$

For a cable force of 10 N, the force at the tip was approximately 1.4 N for this design where a was 2.9 mm, b was 1.7 mm, and d was 0.65 mm. The maximum area of the forceps in contact with tissue during a biopsy was 0.3756 mm².

$$P_{contact} = \frac{F_{tip}}{A_{contact}} \quad (2)$$

Assuming an even distribution of force, the applied pressure was approximately 3.75 MPa. However, by taking a smaller "bite", the contact area was reduced and the pressure can be drastically increased and the required force was decreased.

Figure 2B:
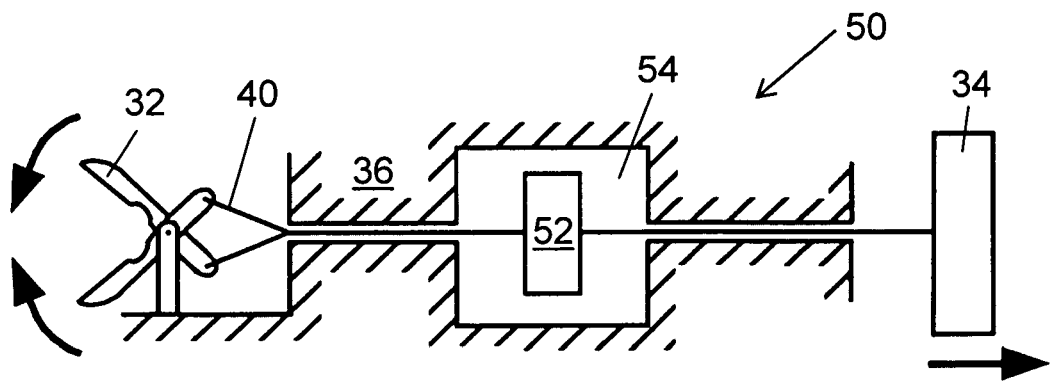

The normal biopsy device 50 depicted in FIG. 2A was modified to contain a load cell 52 to measure clamping forces indirectly, as shown in FIG. 2B. The modifications made to this tool included cutting the tube 36 and wires 40 to place a load cell 52 in series with the wires 40 to measure tensile force when the wires 40 were actuated as shown in FIG. 2B. A plastic case 54 was built to connect the two free ends of the tube to retain the structure of the system, while the wires 40 were affixed to the free ends of the load cell 52. Using this design, the force in the cable was measured. Along with the above model the force at the tip of the grasper was estimated while sampling sets of in vivo tissue using a porcine model.

Figure 3A:
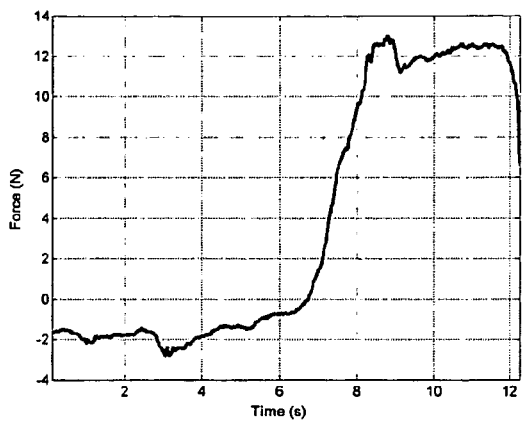
FIG. 3 shows measured cable force to biopsy in vivo porcine hepatic tissue (FIG. 3A) and measured extraction force to biopsy ex vivo bovine liver (FIG. 3B).

Measurements of cable force were made while sampling liver, omentum, small bowel and the abdominal wall of an anesthetized pig. Representative results for a liver biopsy are shown in FIG. 3A. The initial negative offset was due to the slight compression in the cable to push the grasper jaws open before biopsy. The average maximum measured force to biopsy porcine liver for three samples was 12.0±0.4 N. These results are consistent in magnitude with other published results (Chanthasopeephan, et al. (2003) *Annals of Biomedical Engineering* 31:1372–1382) concerning forces sufficient to cut porcine liver.

Generally, biopsy forceps do not completely sever the tissue. When this is the case, the forceps are gently pulled to free the sample. This extraction force also needs to be produced by a biopsy robot. The magnitude of the extraction force needed to be determined so that a robot could be designed to provide sufficient drawbar force to free the sample.

A laboratory test jig was built to measure the force needed to free a biopsy sample of bovine liver. After clamping the sample with the biopsy forceps, a load cell attached to the handle of the device was gently pulled to free the sample while the tensile force was recorded. Representative results shown in FIG. 3B indicate that approximately 0.6 N of force is needed to extract bovine liver tissue with the use of the biopsy forceps.

Based on the in vivo biopsy force measurement results, the design objectives for the biopsy robot were determined. The biopsy robot would need to produce approximately 0.6 N of drawbar force to free the tissue. The wheel design would also need to traverse the in vivo environment without causing tissue damage. Cable forces near 14 N would be needed to successfully biopsy porcine tissue. Also, a camera system was needed to provide visual feedback to the surgeon for abdominal exploration and assistance during tissue biopsy. Finally, the design would need to be contained in a small robot that can fit through the small entry port.

Figure 4A:
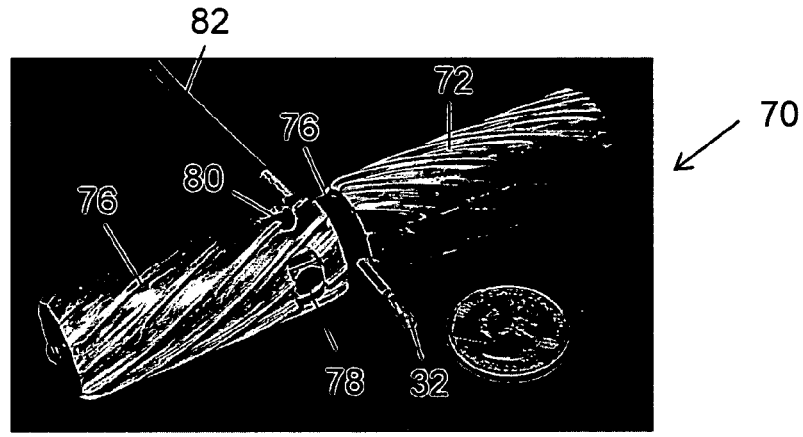
FIGS. 4A and 4B respectively show a photographic image and CAD drawing of a mobile biopsy robot with in vivo imaging capabilities.
Figure 4B:
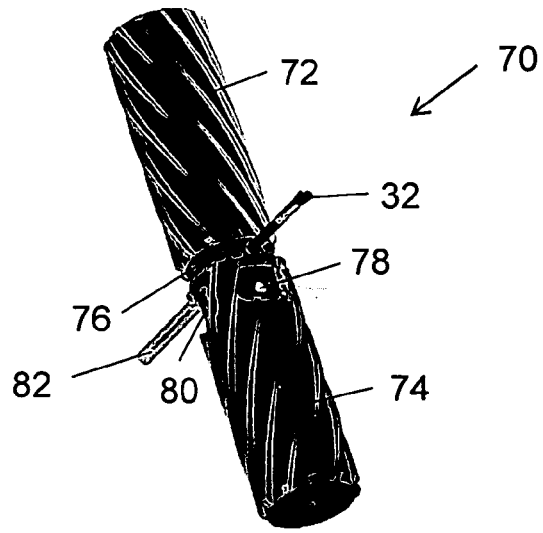

An exemplary biopsy robot was designed. The exemplary robot 70 shown in FIGS. 4A and 4B is cylindrical and is 20 mm in diameter and 100 mm long. It has two independently controlled aluminum wheels 72, 74 attached to two 6 mm diameter permanent magnet direct current motors through a set of bearings and spur gears. The motors are housed in a cylindrical body 76 that also contains the CMOS camera imager, camera lens 78, motor and video control boards, and actuation motor and mechanisms for camera adjustable-focus and biopsy capabilities. The camera and lens 78 are offset to the side to allow space for the biopsy grasper. The wheel 74 on the camera side has slots 80 machined in it to allow for space for the camera lens 78 to see the abdominal environment and the biopsy grasper 32. The camera is capable of focusing at 2 mm to infinity. The inner and outer diameters of the wheel are 17 mm and 20 mm, respectively. The helical profile of the wheels has a pitch of 30° and a grouser depth of 1 mm based on experimental study of wheel performance. The robot 70 has a top speed of approximately 2 cm/s. While the model is tethered for power, wireless models are contemplated.

The robot 70 also has a small appendage 82 attached to prevent the body 76 from spinning. Appendage 82 is spring loaded to retract and provide easy entry through the entry port (e.g., through a laparoscopic surgical tool). At the distal end of this appendage or arm is biopsy forceps 32 used for sampling tissue. The robot's grasper is 2.4 mm wide and can open to 120 degrees.

Figure 3B:
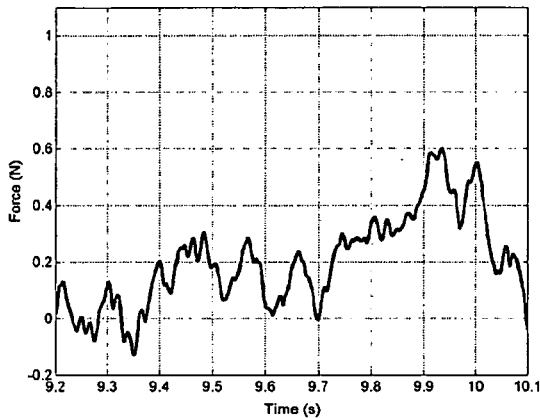
Figure 5:
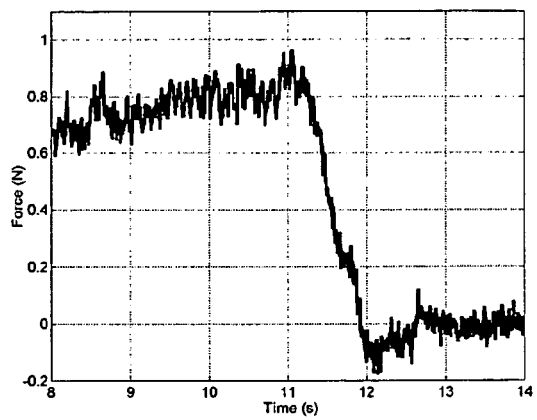
FIG. 5 shows drawbar force production from biopsy robot where maximum drawbar force is produced at 11 seconds, as shown, before slowing down.

As indicated, a complete cut of the tissue is rarely achieved and some tearing of the sample is needed to extract the sample. To obtain a biopsy sample, the in vivo robot should produce enough drawbar force to pull the sample free. The biopsy robot shown in FIGS. 4A and 4B was tested in vivo and with excised bovine liver to measure drawbar forces. The biopsy grasper (tail of the robot) was attached to a stationary load cell. The robot speed was slowly increased as the drawbar force was recorded as shown in FIG. 5. After maximum drawbar force was achieved, around 11 seconds, the robot wheel motion was stopped. Results demonstrated that the robot was capable of producing approximately 0.9 N of drawbar force. This amount of force is 50% greater than the target of 0.6 N in the laboratory measurements (FIG. 3B). This drawbar force is therefore sufficient for sample extraction.

In general, in vivo mobility is difficult because the environment is slick, hilly, and deformable. Moreover, in vivo robots need to traverse the abdominal organs without causing tissue damage. The forces and pressures that cause tissue damage are not well known, but during routine laparoscopic procedures grasping forces as high as 40 N have been recorded (Rosen et al. (2002) *Proc. IEEE International Conference on Robotics and Automation*, Washington, D.C., pp. 1876–1881) with corresponding tissue pressure of approximately 400 kPa. The exemplary in vivo robot weighs only 0.64 N, and is capable of producing a maximum drawbar force of approximately 0.9 N. These forces correspond to an approximate maximum tissue pressure of 1.5 kPa. Therefore, tissue damage will be negligible compared to forces applied by a surgeon during conventional laparoscopic procedures.

Development of an actuation mechanism to drive the biopsy grasper and the camera was achieved through several design iterations and testing. One challenge was transforming the axis of rotation of the motor, which was perpendicular to the tube of the forceps, to a line of translation parallel with the grasper wires.

A first design concept consisted of a series of beveled gears that created a winch system. However, this system required a restoring force such as a spring. The second design concept used a lead screw turned by the motor to power a linkage. This system was prototyped, but failed to produce substantial cable forces.

Figure 6:
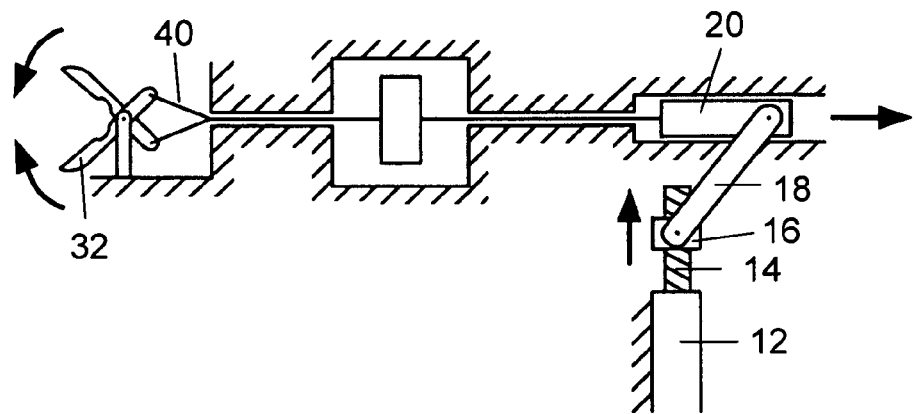
FIG. 6 depicts an actuation mechanism implemented on a biopsy robot for force production measurements.

The lead screw linkage design was reconsidered to increase cable tensile force as shown in the CAD design in FIG. 1 and schematic in FIG. 6. The lead screw 14 was extended through the slider 20. The lead nut 16 was then allowed to translate far enough so that at the point of grasper 32 closure the linkage 18 approaches a mechanism singularity where output force is very large (i.e., at or approaching 0°). The slider 20 is a nearly hollow cylinder and the lead nut 16 and linkage 18 are inside the slider 20 near the singularity. The grasper wires 40 are attached to slider 20 as is either the camera lens or image sensor. This provides the camera an adjustable-focus feature necessary in the in vivo environment.

A direct current motor 12 drives the lead screw 14 vertically as the linkage 18 transforms the vertical motion of the lead nut 16 to the horizontal translation of the slider 20. This allows for a large mechanical advantage at the point when the graspers are nearly closed.

The design of FIG. 1 was implemented in a test jig that included a load cell for measuring applied force. As described herein, the load cell was placed in series with the wires to measure tensile forces during grasping. The lead screw causes a nut to translate vertically. A connecting linkage converts the vertical translation into horizontal motion of a slider. The wires that actuate the graspers were affixed to this slider.

Figure 7:
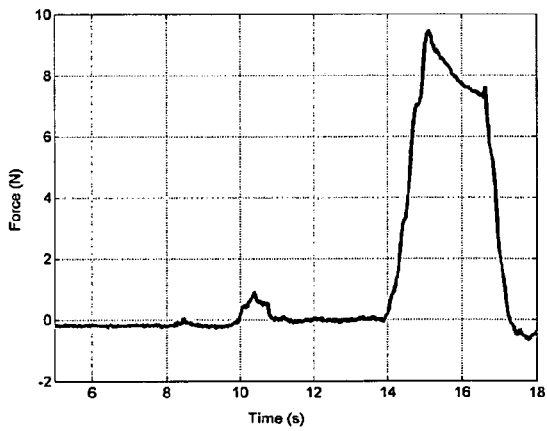
FIG. 7 shows force production measured from the robot biopsy mechanism.

Force measurements were made in the laboratory to determine the maximum amount of force that could be produced using the biopsy robot design. Representative results from these tests are shown in FIG. 7. The average maximum force produced for three samples was 9.6±0.1 N. This force was about 16% smaller than the 12 N measured during in vivo testing. However, the 12 N merely represents the force that was applied. It does not represent the minimum force required to biopsy the tissue. It is probable that the surgeon performed the biopsy and continued to increase the force and merely "squeezed" the sample. The surgeon applied what was known to be a sufficient force rather than a minimum force. The required force could also be largely reduced by simply taking a smaller biopsy sample. Reducing the contact area by 16% would produce the same applied stress.

In vivo mobility testing with this and other similar prototype robots, indicated that such a wheel design produces sufficient drawbar forces to maneuver within the abdominal environment. In vivo porcine tests showed that the helical wheel design allowed the robot to traverse all of the abdominal organs (liver, spleen, small and large bowel), as well as climb organs two to three times its height. These tests were performed without causing any visible tissue damage. Video recorded during one of the tests was used to reconstruct the path traversed by the robot. The total distance traveled during the test without assistance was approximately 1 m.

After exploring the abdominal environment, the biopsy mechanism was used to acquire three samples of hepatic tissue from the liver of the animal. The robot camera was used to find a suitable sample site. The biopsy graspers were opened and the sample site was penetrated with the biopsy forceps' spike. Then the graspers were actuated. This cut nearly all of tissue sample free. The robot was then driven slowly away from the sample site thereby pulling free the tissue sample. This tissue sample was then retrieved after robot extraction through the entry incision. This demonstrates the success of a one-port biopsy and successful tissue manipulation by an in vivo robot.

What is claimed is:

1. A system with a mobile robot for use inside an animal body during minimally invasive surgery, comprising:
    a laparoscopic surgical tool, wherein the robot is adapted to fit through a port of the laparoscopic surgical tool;
    a body for incorporating components of the robot;
    a mobilization element coupled to the body for moving the body of the robot within the animal body, the mobilization element comprising two wheels disposed along a longitudinal dimension of the body and having an axis of rotation substantially parallel to the longitudinal dimension;
    a member disposed between the two wheels and extending from the body in a direction substantially perpendicular to the axis of rotation of the two wheels for converting rotational motion of the wheels into translational motion of the body;
    a controller for controlling remotely the mobilization element;
    an actuator coupled to the controller and mobilization element, the actuator configured to provide movement to the mobilization element based on input from the controller;
    a power supply adapted to power the actuator; and
    a means for obtaining a biopsy sample.

2. The system of claim 1, further comprising at least one imaging device proximate the body of the robot for imaging within the animal body.

3. The system of claim 1, wherein the body is shaped like a cylinder.

4. The system of claim 1, wherein the wheels have treads.

5. The system of claim 1, further comprising a transmitter and receiver for sending data and inputting command signals between the robot and a remote location.

6. The system of claim 1, further comprising at least one sensor that is selected from at least one member of the group consisting of a pH sensor, a temperature sensor, a sensor to detect gasses, a sensor to detect electrical potential, a sensor to detect heart rate, a sensor to detect respiration rate, a sensor to detect humidity, and a sensor to detect blood.

7. The system of claim 1, wherein the mobile robot is wireless.

8. The system of claim 2, wherein the imaging device is movable relative to the body of the robot to adjust a position of the imaging device.

9. The system of claim 8, wherein the position is pan, tilt or combinations thereof.

10. A mobile robot for use inside an animal body during minimally invasive surgery, comprising:
    a body for incorporating components of the robot;
    a means for obtaining a biopsy sample;
    a mobilization assembly coupled to the body for actively moving the body of the robot along a surface within an open space inside the animal body, wherein the mobilization assembly comprises two wheels disposed at each end of the body and having an axis of rotation substantially parallel to the length of the robot; and
    a member disposed between the two wheels and extending from the body in a direction substantially perpendicular to the axis of rotation of the two wheels for converting rotational motion of the wheels into translational motion.

11. The mobile robot of claim 10, further comprising at least one imaging device proximate the body of the robot for imaging within the animal body.

12. The mobile robot of claim 10, wherein the mobilization assembly is adapted for use within a cavity external to organs of the animal body, the cavity selected from at least one of an abdominal cavity, a pelvic cavity and a thoracic cavity.

13. The mobile robot of claim 10, wherein the open space is inside an abdominal cavity.

14. The mobile robot of claim 10, wherein the open space is outside of a gastrointestinal tract.

15. The mobile robot of claim 10, wherein the two wheels have treads.

16. The mobile robot of claim 10, wherein a majority of an external surface area of the robot is provided by the wheels.

17. The mobile robot of claim 10, wherein the mobilization assembly enables turning movement of the body and forward and backward movement of the body transverse to the length of the robot.

18. The mobile robot of claim 10, wherein the mobilization assembly is remotely controlled.

19. A method of performing minimally invasive surgery inside an animal body, comprising:
performing an incision in the animal body;
implanting a robot through the incision into an open space inside the animal body, the robot having a remotely controllable mobilization assembly and a means for obtaining a biopsy sample; and
actively moving the robot along a surface inside the animal body within the open space by driving two wheels of the mobilization assembly, wherein the two wheels have an axis of rotation substantially parallel to a length of the robot and are separated form one another along the length of the robot by a member extending in a direction substantially perpendicular to the axis of rotation of the two wheels for converting rotational motion of the wheels into translational motion capable of moving the robot transverse to the length of the robot.

20. The method of claim 19, further comprising viewing images within the animal body with an imaging device.

21. The method of claim 19, further comprising viewing images within the animal body with an imaging device and performing a surgical task by operation of the manipulator arm.

22. The method of claim 19, wherein implanting the robot includes disposing the robot within a cavity external to organs of the animal body, the cavity selected form at least one of an abdominal cavity, a pelvic cavity and a thoracic cavity.

23. The method of claim 19, wherein implanting the robot includes disposing the robot outside of a gastrointestinal tract.

* * * * *